United States Patent [19]

Bristol et al.

[11] Patent Number: 4,607,037

[45] Date of Patent: Aug. 19, 1986

[54] CARDIOTONIC 2(1H)-PYRIDINONES

[75] Inventors: James A. Bristol; Ila Sircar, both of Ann Arbor, Mich.

[73] Assignee: Warner-Lambert Company, Morris Plains, N.J.

[21] Appl. No.: 681,737

[22] Filed: Dec. 14, 1984

Related U.S. Application Data

[60] Division of Ser. No. 515,799, Jul. 22, 1983, Pat. No. 4,503,061, which is a continuation-in-part of Ser. No. 410,803, Aug. 23, 1982, abandoned.

[51] Int. Cl.$^4$ ............................................. A61K 31/445
[52] U.S. Cl. ..................................... 514/278; 514/318; 546/19; 546/194
[58] Field of Search ................... 546/194; 514/318, 278

[56] References Cited

U.S. PATENT DOCUMENTS 3,951,982  4/1976  Goel ................................ 546/194 X Primary Examiner—Richard A. Schwartz
Attorney, Agent, or Firm—Jerry F. Janssen

[57] ABSTRACT

Certain 2(1H)-pyridinones are cardiotonic agents. Methods for their preparation and use are disclosed.

1 Claim, No Drawings

CARDIOTONIC 2(1H)-PYRIDINONES

CROSS-REFERENCE TO RELATED APPLICATIONS

This is a division of application Ser. No. 515,799 filed July 22, 1983, now U.S. Pat. No. 4,503,061, which is a continuation-in-part of application Ser. No. 410,803 filed Aug. 23, 1982, now abandoned.

BACKGROUND OF THE INVENTION

The present invention relates to compounds and pharmaceutical compositions useful in treating heart failure.

More particularly, the present invention concerns certain 2(1H)-pyridinone compounds, methods for preparing such compounds, pharmaceutical compositions containing these compounds, and a method for treating heart failure in a mammal by employing these pharmaceutical compositions.

United Kingdom Patent Application No. 2,070,606, published Sept. 9, 1981, describes certain 2(1H)-pyridinone derivatives and their use as cardiotonic agents.

U.S. Pat. No. 4,313,951 describes certain 3-substituted-6-(lower alkyl)-5-(pyridinyl)-2(1H)-pyridinones and their use as cardiotonic agents.

SUMMARY OF THE INVENTION

In its broadest chemical compound aspect, the present invention concerns substituted 2(1H)-pyridinone compounds having the structural formula I

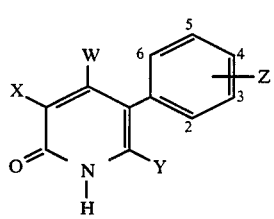

wherein
(A) X is
(1) H, CH$_2$OH, F, Cl, Br, CN,
(2) CO$_2$R$_1$ where R$_1$ is hydrogen, alkyl of from one to six carbon atoms, or a pharmaceutically acceptable metal or amine cation,
(3) CONR$_2$R$_3$ where R$_2$ and R$_3$ are independently hydrogen or alkyl of from one to six carbon atoms, or
(4) NR$_4$R$_5$ where R$_4$ and R$_5$ are independently hydrogen or alkyl of from one to six carbon atoms;
(B) W and Y are independently hydrogen or alkyl of from one to six carbon atoms; and
(C) Z is any of the following groups 1 to 11 attached to the 3- or 4-position of the phenyl ring:
(1)

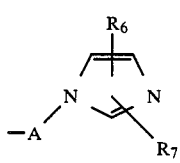

wherein A is a direct bond to the phenyl ring, CH$_2$)$_n$ or O(CH$_2$)$_{n+1}$ (where n is 1 to 4), and R$_6$ and R$_7$ are independently hydrogen, alkyl of from one to six carbon atoms, or hydroxyalkyl of from one to six carbon atoms;

(2)

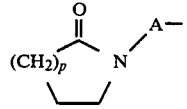

wherein A is as defined above;
(3) NHR$_8$ where R$_8$ is hydrogen, alkyl of from one to six carbon atoms, alkanoyl of from one to six carbon atoms, (CH$_2$)$_n$NH$_2$ where n is from 2 to 6, or SO$_2$R$_9$ where R$_9$ is alkyl of from one to six carbon atoms;
(4)

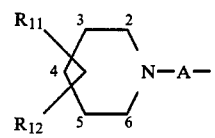

where A is as defined above, and R$_{10}$ is
(a) CH$_2$
(b) oxygen, or
(c) sulfur;
(5)

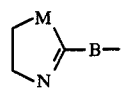

wherein A is defined above and p is from one to three;
(6)

wherein A is as defined above and R$_{11}$ and R$_{12}$ are attached to the same carbon atom of the piperidine ring, which may be carbon number three or four, and wherein when R$_{11}$ is hydrogen, R$_{12}$ is
(a) phenyl,
(b) hydroxy, or
(c) alkoxy of from one to six carbon atoms, and
(d) when R$_{11}$ is not hydrogen, R$_{11}$ and R$_{12}$ taken together are ethylenedioxy;
(7)

wherein B is a direct bond to the phenyl ring or NH, and M is NH, O, or S;
(8)

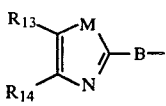

wherein B and M are as defined above, and R₁₃ and R₁₄ are independently hydrogen, alkyl or from one to six carbon atoms,

where R₁₅ is hydrogen or alkyl of from one to six carbon atoms;

(9)

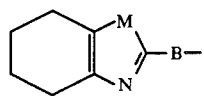

wherein B and M are as defined above;

(10)

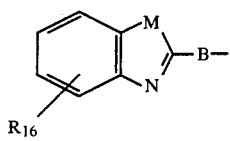

wherein B and M are as defined above, and R₁₆ is hydrogen, hydroxy, alkyl of from one to six carbon atoms, alkoxy of from one to six carbon atoms, —SCH₃, —S(O)CH₃, or —S(O₂)CH₃;

(11)

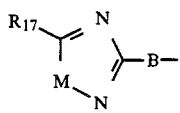

wherein B and M are as defined above, and R₁₇ is hydrogen, alkyl of from one to six carbon atoms, or R₁₈CHOH where R₁₈ is hydrogen or alkyl of from one to six carbon atoms.

In a first subgeneric chemical compound aspect, the present invention is a compound having structural formula I wherein X is hydrogen, hydroxymethyl, fluorine, bromine, or cyano, and the pharmaceutically acceptable salts thereof.

In a second subgeneric chemical compound aspect, the present invention is a compound having structural formula I wherein X is —CO₂R₁ wherein R₁ is hydrogen, alkyl of from one to six carbon atoms, or a pharmaceutically acceptable metal or amine cation.

In a third subgeneric chemical compound aspect, the present invention is a compound having structural formula I wherein X is —CONR₂R₃ where R₂ and R₃ are independently hydrogen or alkyl of from one to six carbon atoms, and the pharmaceutically acceptable salts thereof.

In a fourth subgeneric chemical compound aspect, the present invention is a compound having structural formula I wherein X is —NR₄R₅ wherein R₄ and R₅ are independently hydrogen or alkyl of from one to six carbon atoms, and the pharmaceutically acceptable salts thereof.

In a fifth subgeneric chemical compound aspect, the present invention is a compound having structural formula I wherein Z is

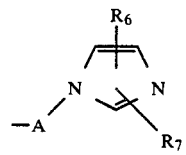

A is a direct bond to the phenyl ring of compound I, (CH₂)ₙ or O(CH₂)ₙ₊₁ (where n is one to four) and R₆ and R₇ are independently hydrogen, alkyl of from one to six carbon atoms, and the pharmaceutically acceptable salts thereof.

In a sixth subgeneric chemical compound aspect, the present invention is a compound having structural formula I wherein Z is

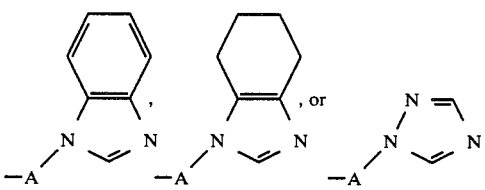

wherein A is a direct bond to the phenyl ring of compound I, (CH₂)ₙ, or O(CH₂)ₙ₊₁ (where n is one to four).

In a seventh subgeneric chemical compound aspect, the present invention is a compound having structural formula I wherein Z is —NHR₈ where R₈ is hydrogen, alkyl of from one to six carbon atoms, alkanoyl of from one to six carbon atoms, (CH₂)ₙNH₂ where n is from two to six, or SO₂R₉ where R₉ is alkyl of from one to six carbon atoms, and the pharmaceutically acceptable salts thereof.

In an eighth subgeneric chemical compound aspect, the present invention is a compound having structural formula I wherein Z is

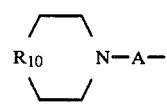

and A is a direct bond to the phenyl ring of compound I, (CH₂)ₙ, or O(CH₂)ₙ₊₁ (where n is one to four), R₁₀ is CH₂, oxygen, or sulfur, and the pharmaceutically acceptable salts thereof.

In a ninth subgeneric chemical compound aspect, the present invention is a compound having structural formula I wherein Z is

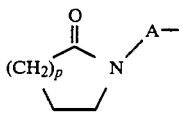

and wherein A is a direct bond to the phenyl ring of compound I, (CH₂)ₙ, or O(CH₂)ₙ₊₁ (where n is one to four), and p is from one to three, and the pharmaceutically acceptable salts thereof.

In a tenth subgeneric chemical compound aspect, the present invention is a compound having structural formula I wherein Z is

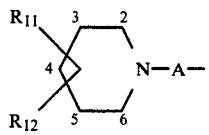

and wherein A is a direct bond to the phenyl ring of compound I, $(CH_2)_n$, or $O(CH_2)_{n+1}$ (where n is one to four), and $R_{11}$ and $R_{12}$ are attached to the same carbon atom of the piperidine ring, which may be carbon number three or four, and wherein when $R_{11}$ is hydrogen, $R_{12}$ is phenyl, hydroxy, or alkoxy of from one to six carbon atoms, and when $R_{11}$ is not hydrogen, $R_{11}$ and $R_{12}$ taken together are ethylene-dioxy, and the pharmaceutically acceptable salts thereof.

In an eleventh subgeneric chemical compound aspect, the present invention is a compound having structural formula I wherein Z is

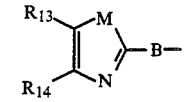

and wherein B is a direct bond to the phenyl ring or NH, and M is NH, O, or S, and the pharmaceutically acceptable salts thereof.

In a twelfth subgeneric chemical compound aspect, the present invention is a compound having structural formula I wherein Z is

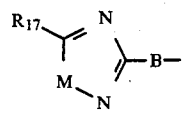

and wherein B is a direct bond to the phenyl ring or NH, and M is NH, O, or S, and $R_{13}$ and $R_{14}$ are independently hydrogen, alkyl of from one to six carbon atoms, $R_{15}$CHOH where $R_{15}$ is hydrogen or alkyl of from one to six carbon atoms, and the pharmaceutically acceptable salts thereof.

In a thirteenth subgeneric chemical compound aspect, the present invention is a compound having structural formula I wherein Z is

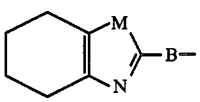

and wherein B is a direct bond to the phenyl ring or NH, and M is NH, O, or S, and the pharmaceutically acceptable salts thereof.

In a fourteenth subgeneric chemical compound aspect, the present invention is a compound having structural formula I wherein Z is

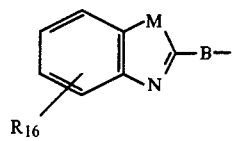

and wherein B is a direct bond to the phenyl ring or NH, and M is NH, O, or S, and $R_{16}$ is hydrogen, hydroxy, alkyl of from one to six carbon atoms, alkoxy of from one to six carbon atoms, $-SCH_3$, $-S(O)CH_3$, or $-S(O_2)CH_3$, and the pharmaceutically acceptable salts thereof.

In a fifteenth subgeneric chemical compound aspect, the present invention is a compound having structural formula I wherein Z is

where B is a direct bond to the phenyl ring or NH, and M is NH, O, or S, and $R_{17}$ is hydrogen, alkyl of from one to six carbon atoms, or $$\underset{R_{18}CHOH}{|}$$

where $R_{18}$ is hydrogen or alkyl of from one to six carbon atoms, and the pharmaceutically acceptable salts thereof.

In its pharmaceutical composition aspect, the present invention is a compound having structural formula I or a pharmaceutically acceptable salt thereof in combination with a pharmaceutically acceptable carrier.

In its pharmaceutical method aspect, the present invention is a method for increasing myocardial contractility and for treating heart failure in a mammal in need of such treatment, which method comprises administering an effective amount of a pharmaceutical composition comprising a compound having structural formula I or a pharmaceutically acceptable salt thereof in combination with a pharmaceutically acceptable carrier.

DESCRIPTION OF THE PREFERRED EMBODIMENTS

The compounds of the invention may be prepared by any of several procedures which are considered to be equivalent for purposes of the invention.

In one such procedure, a compound having the structural formula II

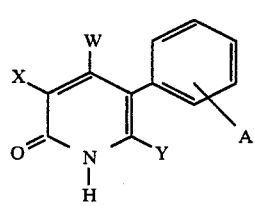

wherein the groups W, X, and Y are as defined above, and A is fluorine, is treated with a compound having the formula Z—H wherein Z is as defined above.

This procedure may be carried out by contacting II and Z—H in the presence of a base such as potassium carbonate at a temperature of from about 200° to 300° C. until the reaction is substantially completed. A period of about 24-36 hours is usually sufficient. The presence of a catalyst such as copper/copper (I) iodide is beneficial.

The starting compounds of structural formula II (where W=hydrogen) may be prepared by methods familiar to those skilled in the art. For example, a fluorophenyl-2-alkanone (or fluorophenylacetaldehyde) may be condensed with N,N-dimethylformamide dimethyl acetal to produce the corresponding 1-(fluorophenyl)-2-(dimethylamino)ethenyl alkanone (alkanal). Treatment of the so produced alkanone (alkanal) with cyanoacetamide under basic conditions will produce the correspondingly substituted compound of Formula II wherein X is CN. This procedure may be performed substantially as described in British Patent Application No. 2,070,606 published Sept. 9, 1981, and in U.S. Pat. No. 4,313,951. The CN group of the thus produced compounds may be converted to other X groups when desired by methods known to those skilled in the art.

In an alternative procedure, a compound having the structural formula III

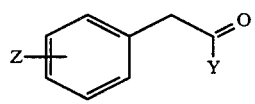

III wherein Y and Z are as defined above, is converted to a compound of the present invention by procedures substantially similar to those above for the conversion of the fluorophenyl-2-alkanone (fluorophenyl-acetaldehyde) to the compound of structure II. That is to say, a compound having structural formula III is reacted with N,N-dimethylformamide dimethyl acetal or a substituted N,N-dimethylforamide diemthyl acetal of formula IV

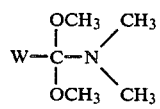

IV (wherein W is as defined above) to produce the corresponding 1-(fluorophenyl)-2-(diemthylamino)ethenyl alkanone (or alkanal). Treatment of the resulting alkanone or alkanal with cyanoacetamide under basic conditons produces the corresponding substituted compound of formula I where X is cyano.

The cyano group of the compound produced by this method is converted to other X groups (where X is as defined above) by methods well known to those skilled in the art.

The usefulness of the compounds of the present invention as cardiotonic agents is demonstrated by their effectiveness in standard pharmacological test procedures, for example, in causing a significant increase in the myocardial contractility in the pentobarbital-anesthitized dog with low or minimal changes in heart rate and blood pressure. This test procedure is described in the following paragraphs.

Test for In Vivo Myocardial Inotropic Activity in Anesthetized Dog

This screen consists of determining the effects of increasing intravenous doses of compound on myocardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administering test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 mg/kg over a period of one minute.

When tested by the above-described Anesthetized Dog Procedure, the compounds of the present invention when administered intravenously at a rate of about 0.01 to 0.31 mg/kg/minute cause dose related significant increases in cardiac contractility with only low or minimal changes in heart rate and blood pressure.

Representative results from these tests for compounds in accordance with the present invention are presented in the following table. The compounds tested had structures corresponding to structure I, with the substituent groups W, X, Y, and Z given in the Table.

TABLE

| Example | W | X | Y | Z | Dose mg/kg Body Weight | % Change in Myocardial Contractility | % Change in Heart Rate | % Change in Blood Pressure |
|---|---|---|---|---|---|---|---|---|
| 1 | Hydrogen | Cyano | Methyl | 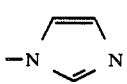 | 0.01 | 39 | 3 | −1.5 |
| | | | | | 0.03 | 116 | 26 | −7.0 |
| | | | | | 0.10 | 136 | 38 | −19.5 |
| | | | | | 0.3 | 139 | 54 | |

TABLE-continued

| Example | W | X | Y | Z | | Dose mg/kg Body Weight | % Change in Myocardial Contractility | % Change in Heart Rate | % Change in Blood Pressure |
|---|---|---|---|---|---|---|---|---|---|
| 2 | Hydrogen | Hydrogen | Methyl | 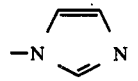 | | 0.01 | 36 | 3 | 3 |
|   |   |   |   |   | | 0.03 | 85 | 9 | 3 |
|   |   |   |   |   | | 0.10 |    | 17 | 11 |
|   |   |   |   |   | | 0.31 |    | 26 | 20 |
| 3 | Hydrogen | Amino | Methyl | 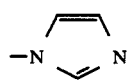 | | 0.01 | 23 | 1 | 1 |
|   |   |   |   |   | | 0.03 | 71 | 6 | 4 |
|   |   |   |   |   | | 0.10 |    | 14 | 12 |
|   |   |   |   |   | | 0.31 | 84 | 19 | 24 |
|   |   |   |   |   | | 1.00 |    | 16 | 30 |
| 4 | Hydrogen | Cyano | Methyl | 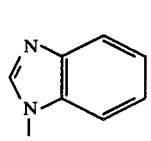 | | 0.01 | 6 | 5 | 4 |
|   |   |   |   |   | | 0.03 | 8 | 10 | 4 |
|   |   |   |   |   | | 0.10 | 8 | 11 | 5 |
|   |   |   |   |   | | 0.31 | 1 | 11 | 5 |
|   |   |   |   |   | | 1.00 | 12 | 9 | 10 |

The compounds of the invention form pharmaceutically acceptable salts with organic and inorganic acids. Examples of suitable acids for salt formation are hydrochloric, sulfuric, phosphoric, boric, methanesulfonic, and the like. The salts are prepared by contacting the free base form with a sufficient amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl and acyl (alkanoyl) groups contemplated by the invention comprise both straight and branched carbon chains of from one to above six carbon atoms. Representative of such groups are methyl, ethyl, isopropyl, pentyl, 3-methylpentyl, methanoyl, ethanoyl, propanoyl, 2-ethylpropanoyl, and the like. Preferred are methyl, ethyl, and ethanoyl.

The compounds of the invention comprise a Z-substituted phenyl group which substituent, Z, may be located at either the 2-, 3-, or 4-position of the benzene ring. More preferably, Z is located at either the 3- or 4-position of the benzene ring. Most preferably Z is located at the 4-position of the benzene ring.

The compounds of the invention can be prepared and administered in a wide variety of oral and parenteral dosage forms. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting was, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Liquid preparations can also be formulated in solution in aqueous polethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as cardiotonic agents, the compounds utilized in the pharmaceutical method of this invention are administered at the initial dosage of about 0.001 mg to about 1.0 mg per kilogram daily. A daily dose range of about 0.01 mg to about 0.5 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if reached.

The following nonlimiting examples illustrate the inventors' preferred methods for preparing the compounds of the invention.

EXAMPLE 1

1,2-Dihydro-5-[4-(1H-imidazol-1-yl)phenyl]-6-methyl-2-oxo-3-pyridinecarbonitrile A mixture of 1,2-dihydro-5-(4-fluorophenyl)-6-methyl-2-oxo-3-pyridinecarbonitrile (5.0 grams), imidazole (25 grams), potassium carbonate (5 grams), copper (0.5 grams) and copper (I) iodide (0.5 grams) is heated just at 200° C. for 24 hours and then at 260° C. for 8 hours. After cooling, the reaction mixture is diluted with water and filtered. The filtrate is acidified with 6 N hydrochloric acid and the precipitate is collected. This solid is boiled in 1 liter of methanol and the hot mixture is filtered. The filtrate is evaporated to a volume of 200 ml and cooled to give 0.7 grams of 1,2-dihydro-5-[4-(1H-imidazol-1-yl)phenyl]-6-methyl-2-oxo-3-pyridinecarbonitrile: mp 300°–301° C.

EXAMPLE 2

1,2-Dihydro-5-[4-(1H-imidazol-1-yl)phenyl]-6-methyl-2-oxo-3-pyridinecarbonitrile (Alternative Procedure)

A mixture of 1-[4-[(1H-imidazol-1-yl)phenyl]-2-propanone (1.0 grams) and N,N-dimethylformamide diethyl acetal (10 ml) in 20 ml of acetonitrile is allowed to stir overnight. The mixture is concentrated on a rotary evaporator and the residue is dissolved in 20 ml of N,N-dimethylformamide and treated with 0.46 grams of cyanoacetamide and 0.6 grams of sodium methoxide. This mixture is heated under reflux for five minutes, cooled, and concentrated on the rotary evaporator. The residue is suspended in water (40 ml) and the solid material is collected and recrystallized from 2-propanol to give 0.2 grams of 1,2-dihydro-5-[4-(1H-imidazol-1-yl)phenyl]-6-methyl-2-oxo-3-pyridinecarbonitrile: mp 298°–300° C.

EXAMPLE 3

1,2-Dihydro-5-(4-fluorophenyl)-6-methyl-2-oxo-3-pyridinecarbonitrile

A mixture of 4-fluorophenyl acetone (50 grams) and 162.5 ml of N,N-dimethylformamide dimethyl acetal in 75 ml of acetonitrile is stirred for 12 hours and then the reaction mixture is concentrated on a rotary evaporator. The residual solid is suspended in 100 ml of hexane and filtered to give 59.6 grams of 1-(4-fluorophenyl)-2-(dimethylamino)ethenyl-2-propanone.

A mixture of 1-(4-fluorophenyl)-2-(dimethylamino)ethenyl-2-propanone (59.6 grams), cyanoacetamide (26.7 grams) and sodium methoxide (34.3 grams) in 830 ml of dimethylformamide is heated under reflux for two hours and then the reaction mixture is concentrated on a rotary evaporator. The residual solid is suspended in water (2 liters) and is stirred overnight. The aqueous mixture is acidified with 12 N HCl, diluted with water to a volume of 4 liters, and stirred for two hours. The solid product is collected, washed with water (500 ml) and then with ethanol to give 55.4 grams of 1,2-dihydro-5-(4-fluorophenyl)-6-methyl-2-oxo-3-pyridinecarbonitrile.

EXAMPLE 4

1-[4-(1H-Imidazol-1-yl)phenyl]-2-propanone

A mixture of 34.5 grams 1-[4-1H-imidazol-1-yl)-phenyl carboxaldehyde (prepared according to the general methods of L. M. Sitkina and A. M. Simonov, Khim. Geterotsikl. Soedin. Akad. Nauk. Latv. SSR, 143 (1966) - Chem. Abstr. 65, 13686 (1966)), 150 ml of nitroethane, and 8.3 grams of ammonium acetate is heated under reflux for 60 hours. Upon cooling, the reaction mixture is concentrated on the rotary evaporator and finally dried under high vacuum. The residue containing 1-[4-(1H-imidazol-1-yl)phenyl]-2-nitropropene as a mixture of stereoisomers is used without purification.

A mixture of 1-[4-(1H-imidazol-1-yl)phenyl]-2-nitropropene prepared above, iron powder (94.7 grams), and hydrated iron (III) chloride (1.2 grams) in 50 ml of methanol and 170 ml of water is heated to reflux and treated dropwise with 85 ml of 12 N hydrochloric acid over four hours. After heating under reflux for one additional hour, the reaction mixture is cooled, and filtered. The filtrate is made basic with 40% ammonium hydroxide solution and the entire mixture is extracted thoroughly with ethyl acetate. The ethyl acetate is treated with charcoal, dried (magnesium sulfate) and concentrated on the rotary evaporator to give a dark yellow oil. This material is chromatographed on a Waters Prep 500A, using silica gel and eluting with 2% methanol in chloroform. The main fraction contains 1-[-4-(1H-imidazol-1-yl)-phenyl]-2-propanone.

EXAMPLE 5

1-[4-(2-Nitro-1-propenyl)phenyl]-1H-imidazole

A mixture of 292 g (1.70 mole) of 4-(1H-imidazol-1-yl)benzaldehyde, 153.7 g (1.97 mole) of nitroethane (96%), and 15.4 g (.173 mole) of β-alanine in 1000 ml n-butanol is refluxed for nine hours. The reaction mixture is allowed to cool overnight, the solid collected, and washed successively with ether and water to give 78.7 g of dark yellow crystals, mp 119°–120° C. Concentration of the filtrate to approximately 500 ml and cooling at 0° gave a second crop (87.2 g) of the product, mp 116°–118° C.

Evaporation of all the solvent gave a red oil, which crystallized upon standing a few days. This is diluted with n-butanol (200 ml), the mixture cooled in the refrigerator, and the solid collected and washed as above when 44.7 g of dark yellow powder is obtained, mp 110°–117° C. [Prepared according to the general methods of L. M. Sikkina and A. M. Simonov, Khim. Geterotsikl. Soedin. Akad. Nauk. Latv. SSR, 143 (1966)—Chem. Abstr. 65, 13686 (1966)].

EXAMPLES 6-8

Similarly reaction of p-fluorobenzaldehyde with 4,5,6,7-tetrahydro-1H-benzimidazole) benzimidazole and 4-phenyl piperidine gave 1-[4-(4,5,6,7-tetrahydro-1H-benzimidazol-1-yl)phenyl]carboxaldehyde, mp 104°-110° C., 1-[4-1H-benzimidazol-1-yl]phenyl]-carboxaldehyde, mp 96.5°-98° C., and 1-[4-(4-phenyl-piperidin-1-yl)phenyl]carboxaldehyde, mp 117°-119° C.

EXAMPLES 9-13

Following the procedure described in Example 5 but using suitably substituted benzaldehyde, one obtains the following nitropropenes;
1-[4-(2-nitro-1-propenyl)phenyl]-1H-1,2,4-triazole, mp 141.5°-142.5° C.;
1-[4-(2-nitro-1-propenyl)phenyl]-4,5,6,7-tetrahydro-1H-benzimidazole;
1-[4-(2-nitro-1-propenyl)phenyl]-benzimidazole, mp 147°-149° C.;
1-[4-(2-nitro-1-propenyl)phenyl]-acetamide;
1-[4-(2-nitro-1-propenyl)phenyl]-4-phenylpiperidine, mp 148°-149° C.

EXAMPLE 14

1-[4-(1H-Imidazol-1-yl)phenyl]-2-propanone

A 5.0 liter 3-neck flask fitted with a condenser, addition funnel, and mechanical stirrer is charged with a mixture of 218.4 g (0.954 mole) of 1-[4-(2-nitro-1-propenyl)phenyl-1H-imidazole, 449 g (8.04 mole) of iron powder (325 mesh), 6.4 g of FeCl$_3$6H$_2$O, 350 ml of methanol and 760 ml of water. The mixture is heated to reflux with stirring and 450 ml of concentrated hydrochloric acid is added dropwise over a period of 2.5 hours. Refluxing is continued for two to three hours. The reaction mixture is cooled to room temperature, 1.9 liter of CH$_2$Cl$_2$ was added, and the mixture stirred rapidly for one hour. This is filtered, the inorganic solid is washed three times with 500 ml portions of CH$_2$Cl$_2$, and the layers separated. The CH$_2$Cl$_2$ layer is dried over MgSO$_4$, then filtered through a bed of silica gel (600 g, 70-230 mesh), which is washed with 5 liters of CH$_2$Cl$_2$ and then with 13 liters of 10% methanol in methylene chloride. Evaporation of the solvent gave 126.7 g of a brown oil which crystallized on standing. The product is purified via the sodium bisulfate addition product to give a product having a mp of 71.5°-72.5° C.

EXAMPLES 15-19

Following the procedure described in Example 14 but using suitably substituted nitropropenes, one obtains the following propanones:
1-[4-(1H-1,2,4-triazol-1-yl)phenyl]-2-propanone, mp 97°-98.5° C.;
1-[4-(4,5,6,7-tetrahydro-1H-benzimidazol-1-yl)phenyl]-2-propanone, mp 105°-108° C.;
1-[4-(1H-benzimidazol-1-yl)phenyl]-2-propanone,
1-[4-(acetamido)phenyl]-2-propanone, mp 118°-120° C.;
1-[4-(4-phenyl-1-piperidinyl)phenyl]-2-propanone, mp 92°-93° C.

EXAMPLE 20

1,2-Dihydro-6-methyl-2-oxo-5-[4-(1H-imidazol-1-yl)phenyl]-3-pyridine carbonitrile A solution of 125.3 g (0.626 mole) of 1-[4-(1H-imidazol-1-yl)phenyl]-2-propanone and 134.2 g of (1.13 mole; 1.8 equivalents) dimethylformamide dimethyl acetal in 1 liter of acetonitrile, is stirred for 18 hours at room temperature and the resulting mixture is heated to reflux for 1.5 hours to complete the reaction. After evaporation of the solvent, the residue is dissolved in 600 ml of CH$_2$Cl$_2$ and the solution is filtered through a bed of silica gel (300 g, 230-400 mesh) which is then washed with 3.0 liters of CH$_2$Cl$_2$ and then with 3.0 liters of 5% methanol in methylene chloride. Evaporation of the solvent gave 132 g of a dark, dark brown solid which is used directly without any purification.

To a mixture of 132 g (0.514 mole) of the above N,N-dimethylaminoethenyl methyl ketone and 47.5 g (0.565 mole) of 2-cyanoacetamide dissolved in 800 ml of N,N-dimethylformamide is added with stirring 62.0 g (1.15 mole) of sodium methoxide and the resulting reaction mixture is heated to 120° and maintained at that temperature for three hours. The reaction mixture is concentrated in vacuo on a rotary evaporator. The concentrate is treated with about 600 ml of CH$_3$OH and 100 ml of acetic acid and the suppension is stirred for 15-30 minutes. After cooling in ice, the rust-colored solid is collected and washed with CH$_3$OH followed by ether to afford 65.8 g of the product, mp 295°-296.5° C., dec.

One gram of this material was recrystallized from 10 ml of dimethylformamide to give 0.70 g of analytically pure material, mp 306°-307° C., dec.

EXAMPLES 21-24

Following the procedure described in Example 20, but substituting suitably substituted propanones one obtains the following pyridones:
1,2-dihydro-6-methyl-2-oxo-5-[4-(1H-1,2,4-triazol-1-yl)phenyl]-3-pyridine carbonitrile, mp 309°-310° C. (dec)
1,2-dihydro-6-methyl-2-oxo-5-[4-(4,5,6,7-tetrahydro-1H-benzimidazol-1-yl)phenyl]-3-pyridine carbonitrile, mp>350° C.;
1,2-Dihydro-6-methyl-2-oxo-5-[4-1H-benzimidazol-1-yl)-phenyl]-3-pyridine carbonitrile, mp 350°-353° C. (dec);
N-[4-(5-cyano-1,6-dihydro-2-methyl-6-oxo-3-pyridinyl)phenyl]-acetamide, mp 312°-314° C. (dec);

EXAMPLE 25

1,2-Dihydro-6-methyl-2-oxo-5-[4-(1H-imidazol-1-yl)phenyl]-3-pyridine-carbonitrile, monohydrochloride To a suspension of 55.8 g of 1,2-dihydro-6-methyl-2-oxo-5-[4-(1H-imidazol-1-yl)phenyl]-3-pyridine carbonitrile in 500 ml of 10% aqueous methanol is added concentrated hydrochloric acid with stirring to a pH of 2. After cooling at 0° C. overnight, the solid is collected, washed with cold methanol followed by ether, and dried in vacuo at 120° for two hours to give 62.6 g of the monohydrochloride as light beige powder, mp 322°-326° C., dec.

EXAMPLE 26

4-(Dimethylamino)-3-[4-(4-phenyl-1-piperidinyl)-phenyl]-3-buten-2-one

A mixture of 4.0 g of 1-[4-(4-phenyl-1-piperidinyl)-phenyl]-2-propanone and 16 ml of dimethylformamide dimethylacetal is stirred at room temperature overnight, followed by heating at 45°-60° C. for six hours. The solvent is evaporated and the residue triturated with two 100 ml portions of hexane. The solid is filtered and dried to give 3.5 g of orange powder, mp 93°–100° C. Upon standing overnight at 0° C., the filtrate gave an additional 0.7 g of the product, mp 103.5°–105° C. This material is used directly for the next step without further purification.

EXAMPLE 27

1,2-Dihydro-6-methyl-2-oxo-5-[4-(4-phenyl-1-piperidinyl)phenyl]-3-pyridinecarboxamide A mixture of 2.6 g of 4-(dimethylamino)-3-[4-(4-phenyl-1-piperidinyl)phenyl]-3-buten-2-one, a mixture of 0.75 g of cyanoacetamide, 0.8 ml of piperidine acetate in 25 ml of acetonitrile is refluxed for 24 hours. The solid is collected, washed with $CH_3CN$, ether, and dried to give 0.80 g beige solid, mp 335°–338° C. (d).

EXAMPLE 28

1,2-Dihydro-6-methyl-2-oxo-5-[4-(4-phenyl-1-piperidinyl)phenyl]-3-pyridine carbonitrile A mixture of 0.9 g (0.00232 mole) of 1,2-dihydro-6-methyl-2-oxo-5-[4-(4-phenyl-1-piperidinyl)phenyl]-3-pyridinecarboxamide, 1.8 g of $P_2O_5$, and 10 ml of dimethylformamide was refluxed for one hour, cooled to room temperature, and poured into 100 ml of water. The solution was adjusted to pH 6.7 with $NH_3$ and the solid collected. After recrystallizing twice from MeOH (using charcoal treatment), 105 mg of a light brown solid was obtained. Approximately 80 mg of this solid was stirred overnight in 5 ml of saturated $NaHCO_3$ (to which two drops of MeOH were added), then it was collected, washed, and dried. Sixty one mg of light brown solid was obtained.

EXAMPLE 29

5-[4-(1H-Imidazol-1-yl)phenyl]-6-methyl-2(1H)-pyridinone

A solution of 1,2-dihydro-5-[4-(1H-imidazol-1-yl)phenyl]-6-methyl-2-oxo-3-pyridinecarbonitrile 21.8 g) in 110 ml of 85% (w/w) sulfuric acid is heated at 205° C. for 19 hours. The reaction mixture is cooled to room temperature, poured into 600 ml of ice, and the resulting solution adjusted to pH 8 with concentrated ammonia. The precipitate is collected and recrystallized from dimethylformamide to give 10.0 g of 5-[4-(1H-imidazol-1-yl)phenyl]-6-methyl-2(1H)-pyridinone, mp 310°–314° C.

EXAMPLE 30

3-Bromo-5-[4-(1H-imidazol-1-yl)phenyl]-6-methyl-(1H)-pyridinone

A solution of 5-[4-(1H-imidazol-1-yl)phenyl]-6-methyl-2(1H)-pyridinone (9.9 g) in 120 ml of acetic acid is treated dropwise with a solution of 2.15 g of bromine in 16 ml of acetic acid over a period of 1.5 hours, keeping the reaction temperature at 75°–80° C. The reaction mixture is heated for one more hour at 75°–80° C., cooled to room temperature, and then cooled in an ice bath. The yellow precipitate is collected, washed with acetic acid, suspended in 100 ml of water, and neutralized with 50% aqueous ammonia. The resulting cream colored solid is collected, recrystallized from dimethylformamide, and chromatographed using silica gel (300 g) and eluting with 10% methanol in dichloromethane to give 1.15 g of 3-bromo-5-[4-(1H-imidazol-1-yl)-phenyl[6-methyl-2(1H)-pyridinone, mp 303.5°–305° C. (dec).

EXAMPLE 31

3-Amino-5-[4-(1H-imidazol-1-yl)phenyl]-6-methyl-2(1H)-pyridinone

A solution of 1,2-dihydro-5-[4-(1H-imidazol-1-yl)phenyl]-6-methyl-2-oxo-3-pyridinecarbonitrile (5.0 g) in 25 ml of concentrated sulfuric acid is heated on a steam bath for 40 minutes, cooled to room temperature and poured into 150 ml of ice. The mixture is adjusted to pH 8 with concentrated ammonia. The solid is collected and recrystallized successively from 10:1 water/acetic acid, dimethylformamide, and 2-methoxyethanol to give 2.06 g of 1,2-dihydro-5-[4-(1H-imidazol-1-yl)phenyl]-6-methyl-2-oxo-3-pyridinecarboxamide, mp 311°–315° C. (dec).

A mixture of 1,2-dihydro-5-[4-(1H-imidazol-1-yl)phenyl]-6-methyl-2-oxo-3-pyridinecarboxamide (1.48 g) prepared above, 1.3 g sodium hydroxide, and 50 ml of water is cooled in ice and treated dropwise with 0.385 ml bromine over ten minutes. The resulting solution is heated on a steam bath for 45 minutes, cooled to room temperature, and neutralized with 6 N hydrochloric acid. The solid is collected, treated with 20 ml of 1.0 N HCl, filtered, and the filtrate neutralized with concentrated ammonia. This solid is collected, dried, and chromatographed using silica gel (35 g) and eluting with 10% methanol in dichloromethane to give 0.26 g of 3-amino-5-[4-(1H-imidazol-1-yl)phenyl]-6-methyl-2(1H)-pyridinone, mp 302°–304° C. (dec).

I claim:

1. A method of increasing cardiac contractility in a mammal comprising administering to a mammal in need of such treatment a pharmaceutical composition comprising an effective amount of a compound having the structural formula

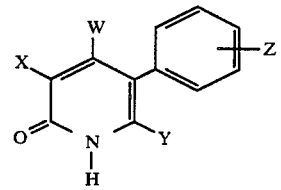

wherein
(A) X is
  (1) H, $CH_2OH$, F, Cl, Br, CN;
  (2) $CO_2R_1$ where $R_1$ is hydrogen, alkyl of from one to six carbon atoms, or a pharmaceutically metal or amine cation;
  (3) $CONR_2R_3$ where $R_2$ and $R_3$ are independently hydrogen or alkyl of from one to six carbon atoms; or
  (4) $NR_4R_5$ where $R_4$ and $R_5$ are independently hydrogen or alkyl of from one to six carbon atoms;
(B) W and Y are independently hydrogen or alkyl of from one to six carbon atoms;
(C) Z is

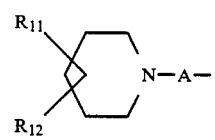

wherein A is a direct bond to the phenyl ring, $(CH_2)_n$ or $O(CH_2)_{n+1}$ where n is an integer of from 1 to 4 and $R_{11}$ and $R_{12}$ are attached to the same carbon atom of the piperidine ring, which may be carbon number three or four, and wherein when $R_{11}$ is hydrogen, $R_{12}$ is (a) phenyl;
(b) hydroxy; or
(c) alkoxy of from one to six carbon atoms, and
when $R_{11}$ is not hydrogen, $R_{11}$ and $R_{12}$ taken together are ethylenedioxy;
or a pharmaceutically acceptable salt thereof.

* * * * *